United States Patent
Jayapathy

(10) Patent No.: US 6,235,722 B1
(45) Date of Patent: May 22, 2001

(54) PHARMACOLOGICAL PREPARATION

(76) Inventor: Balakrishnan Jayapathy, 9 Souris Ct., Minot, ND (US) 58701

( * ) Notice: Subject to any disclaimer, the term of this patent is extended or adjusted under 35 U.S.C. 154(b) by 0 days.

(21) Appl. No.: 09/404,766

(22) Filed: Sep. 24, 1999

(51) Int. Cl.[7] ............................. A61K 31/70; A61K 31/56
(52) U.S. Cl. ............................. 514/31; 514/179; 514/947
(58) Field of Search ............................. 514/31, 179, 947

(56) References Cited

U.S. PATENT DOCUMENTS 5,104,657 * 4/1992 Abdulla .................................. 424/401

* cited by examiner

Primary Examiner—Kevin E. Weddington
(74) Attorney, Agent, or Firm—Beck & Tysver

(57) ABSTRACT

A topical preparation comprising nystatin and hydrocortisone to satisfactory treat fungus infections of the skin in the ear canal.

1 Claim, No Drawings

PHARMACOLOGICAL PREPARATION

FIELD OF THE INVENTION

The present invention relates generally to a pharmacological preparation which has proven to be unusually successful for the treatment of the fungus infections of the skin of the ear canal.

BACKGROUND OF THE INVENTION

Control of the fungus infections is important for many patients. Nystatin, Mycostatin® is commercially available as an oral suspension, topical powder, cream, ointment, and pastille for treatment of yeast and some fungal infections involving the skin, gastrointestinal tract and vagina.

DETAILED DESCRIPTION OF THE INVENTION

The applicant has discovered that a suspension of Mycostatin® in Synalar can provide an effective topical treatment for fungus infections of the skin of the ear canal. Synalar® is a composition whose active ingredient is fluocinolone acetonide. Fluocinolone acetonide is a corticosteroid that has anti-inflammatory, anti-pruritic, and vasoconstrictive properties. In fungus infections of the skin of the ear canal it helps to reduce the swelling of the skin caused by the infection. It helps also to alleviate the intense itching the infection causes. By reducing the swelling of the skin it permits the active antifungal antibiotic Nystatin to enter deep into the ear canal to exert its fungicidal and fungistatic properties. Both ingredients are necessary in the eardrops to successfully treat fungus infections of the ear canal and their associated symptoms of pain, swelling, and itching. Although full range of titration has not been developed excellent clinical performance occurs with the suspension set forth as follows:

Mix the two ingredients, Nystatin and a cortiocosteroid agent such as hydrocortisone in a liquid vehicle. Each ml of the preparation contains a fine suspension of 100,000 units of Nystatin and 10 mg of hydrocortisone in a liquid vehicle with preservatives. The operable range of Nystatin may vary from 25,000 units to 200,000 units. The hydrocortisone may vary from 5 to 20 mg per ml.

DESCRIPTION AND INGREDIENT RATIOS FOR EAR DROPS FOR USE IN FUNGAL INFECTIONS OF SKIN OF EAR CANAL

Fungal infections in the skin of the ear canal are not uncommon. These infections cause severe itching in the ear canal and on occasion pain. The skin of the ear canal can swell to the point where it can affect the hearing. There is so far no satisfactory treatment for fungus infections of the ear canal.

A pharmacological preparation which is a combination of two active ingredients has been found to be successful in the treatment of certain fungus infections in the ear canal. These two ingredients are:

1. Nystatin; and
2. A corticosteroid such as Hydrocortisone

Nystatin is an antifungal antibiotic obtained from Streptomyces Noursei. Nystatin is both fungistatic and fungicidal in vitro against a wide variety of yeasts and yeast-like fungi. Nystatin does not dissolve in water. It is used in the form of a fine suspension.

Hydrocortisone is an anti-inflammatory corticosteroid. It is especially useful for the relief of itching and for reducing the swelling of inflamed tissues.

While the antibiotic Nystatin acts against the fungus causing the infection, the hydrocortisone component of the mixture is active against the symptoms of the itching and swelling.

Each ml of this antifungal preparation for use in fungal infections of the skin of the ear canal contains in suspension, as a fine powder, 100,000 units of Nystatin and 10 mg of hydrocortisone in a vehicle with various inactive ingredients and preservatives.

The amount of Nystatin may range from 25,000 to 200,000 units and the hydrocortisone from 5 mg to 20 mg in each ml of the preparation.

A formulation of Nystatin and hydrocortisone as described above will be a new, unique, and effective method to treat fungal infections in the skin of the ear canal.

Since the preparation is a suspension it needs to be shaken well before each use. It is effective when 4–5 drops of the suspension are instilled in the ear canal three times a day for 10 days. This manner of use results in complete clearing of the fungus infections in 90% of cases.

The above specification examples and data provide a complete description of the manufacture and use of the composition of the invention. Since many embodiments of the invention can be made without departing from the spirit and scope of the invention, the invention resides in the claims hereinafter appended.

I claim:

1. A topical preparation comprising Nystatin and hydrocortisone in a ratio of 25,000 to 200,000 units of Nystatin combined with 5 to 20 mg of hydrocortisone in 1 ml of a liquid vehicle is a new, unique, and satisfactory treatment of fungus infections of the skin in the ear canal.

* * * * *